(12) United States Patent  
Frazier et al.

(10) Patent No.: US 11,583,214 B2  
(45) Date of Patent: Feb. 21, 2023

(54) ADAPTIVE PSYCHOLOGICAL ASSESSMENT TOOL

(71) Applicant: THE CLEVELAND CLINIC FOUNDATION, Cleveland, OH (US)

(72) Inventors: Thomas W. Frazier, Pepper Pike, OH (US); Eric W. Klingemier, Burghill, OH (US); Charles P. Steiner, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 262 days.

(21) Appl. No.: 16/870,946

(22) Filed: May 9, 2020

(65) Prior Publication Data

US 2020/0352499 A1 Nov. 12, 2020

Related U.S. Application Data

(60) Provisional application No. 62/845,728, filed on May 9, 2019.

(51) Int. Cl.
*A61B 5/00* (2006.01)
*A61B 5/16* (2006.01)
*G06F 3/01* (2006.01)

(52) U.S. Cl.
CPC .............. *A61B 5/165* (2013.01); *A61B 5/167* (2013.01); *G06F 3/013* (2013.01)

(58) Field of Classification Search
None
See application file for complete search history.

(56) References Cited

U.S. PATENT DOCUMENTS 6,027,216 A 2/2000 Guyton et al.
10,617,295 B2 * 4/2020 Klin .................. A61B 3/113
(Continued)

FOREIGN PATENT DOCUMENTS

WO 2014/145383 A1 9/2014
WO 2014/186620 A1 11/2014

OTHER PUBLICATIONS

Dris, Alanoud Bin, et al. "Intelligent Gaze-Based Screening System for Autism." 2019 2nd International Conference on Computer Applications & Information Security (ICCAIS). IEEE, 2019.
(Continued)

*Primary Examiner* — Shirley X Jian
(74) *Attorney, Agent, or Firm* — Tarolli, Sundheim, Covell & Tummino LLP (57) ABSTRACT

Systems and methods for performing psychological assessment are provided. An initial visual stimulus is selected and a series of steps are iteratively performed until associated confidence values for each of a plurality of indices meet a threshold value. The selected visual stimulus is provided at the display. Gaze tracking data is received from a remote eye tracking device in response to the selected stimulus being displayed to a patient. A deviation of the gaze tracking data from a standard response is determined. A score and the associated confidence value for at least one of the plurality of indices are adjusted based on the determined deviation of the gaze tracking data from the standard response. A new visual stimulus is selected based on the confidence values of the plurality of indices. Respective scores for the plurality of indices are provided to a user.

19 Claims, 4 Drawing Sheets

(56) References Cited

U.S. PATENT DOCUMENTS

| | | | |
|---|---|---|---|
| 2013/0012790 A1* | 1/2013 | Horseman | G16Z 99/00 600/301 |
| 2014/0108309 A1* | 4/2014 | Frank | G06Q 50/01 706/12 |
| 2014/0323817 A1* | 10/2014 | el Kaliouby | G16H 20/40 600/300 |
| 2016/0022136 A1 | 1/2016 | Ettenhofer et al. | |
| 2016/0055236 A1* | 2/2016 | Frank | G06F 40/35 707/748 |
| 2016/0262613 A1 | 9/2016 | Klin et al. | |
| 2017/0319123 A1 | 11/2017 | Voss et al. | |

OTHER PUBLICATIONS

Frazier, Thomas W., et al. "Development of an objective autism risk index using remote eye tracking." Journal of the American Academy of Child & Adolescent Psychiatry 55.4 (2016): 301-309.

PCT International Search Report and Written Opinion for corresponding International Application Serial No. PCT/US2020/032270, dated Aug. 24, 2020, pp. 1-17.

\* cited by examiner

ADAPTIVE PSYCHOLOGICAL ASSESSMENT TOOL

RELATED APPLICATIONS

This application claims priority from U.S. Provisional Patent Application Ser. No. 62/845,728, titled "Adaptive Psychological Assessment Tool and filed May 9, 2019, the entire contents of which are hereby incorporated by reference.

TECHNICAL FIELD

The present disclosure relates generally to psychological assessment and, more specifically, to an adaptive psychological assessment tool.

BACKGROUND

Currently, the medical standard for measuring symptoms of various psychological conditions, including Autism Spectrum Disorder (ASD), includes one or more qualitative and/or subjective measurements. However, qualitative and/or subjective measurements can be influenced by subjective perceptions and skewed by rater bias. Quantitative, objective measurements would not be influenced by subjective perspectives or skewed by rater bias and, instead, provide an objective risk marker for an associated psychological condition. Patients with these psychological conditions often exhibit deficits in eye gaze, which can be measured quantitatively using eye tracking technology.

SUMMARY

In one example, a non-transitory computer readable medium stores machine-readable instructions that are executable by a processor. The machine-readable instructions include a user interface, a tracker interface, a data analyzer, and a stimulus selector. The user interface provides a selected visual stimulus to a patient. The tracker interface receives gaze tracking data from a remote eye tracking device in response to the selected stimulus being displayed to a user. The data analyzer determines a deviation of the gaze tracking data from a standard response and adjusts a score and the associated confidence value for at least one of a plurality of indices based on the determined deviation of the gaze tracking data from the standard response. The stimulus selector selects a new visual stimulus based on the confidence values of the plurality of indices.

In another example, a method is provided. An initial visual stimulus is selected and a series of steps are iteratively performed until associated confidence values for each of a plurality of indices meet a threshold value. The selected visual stimulus is provided at the display. Gaze tracking data is received from a remote eye tracking device in response to the selected stimulus being displayed to a patient. A deviation of the gaze tracking data from a standard response is determined. A score and the associated confidence value for at least one of the plurality of indices are adjusted based on the determined deviation of the gaze tracking data from the standard response. A new visual stimulus is selected based on the confidence values of the plurality of indices. Respective scores for the plurality of indices are provided to a user.

In yet another example, a system includes a display, a non-transitory memory storing machine-readable instructions, and a processor that accesses the non-transitory memory and executes the machine-readable instructions. The machine-readable instructions include a user interface, a tracker interface, a data analyzer, and a stimulus selector. The user interface provides a selected visual stimulus to a patient. The tracker interface receives gaze tracking data from a remote eye tracking device in response to the selected stimulus being displayed to a user. The data analyzer determines a deviation of the gaze tracking data from a standard response and adjusts a score and the associated confidence value for at least one of a plurality of indices based on the determined deviation of the gaze tracking data from the standard response. The stimulus selector selects a new visual stimulus based on the confidence values of the plurality of indices.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "psychological condition" can refer to any mental condition in which the qualities of a mental state are relatively constant even though the state itself may be dynamic. Accordingly, evaluation of a psychological condition includes, but is not limited to, identifying and quantifying a manifestation of a mental or behavioral dysfunction, and can include identification and quantification personality traits, cognitive or language processes, and other non-pathological psychological processes.

Examples of psychological conditions that do represent mental or behavioral dysfunction can include autism spectrum disorder (ASD), anxiety disorder, attention deficit hyperactivity disorder (ADHD), and language disorders.

As used herein, the term "psychological assessment" can refer to the attempt of a skilled medical professional to use the techniques and tools of psychology to diagnose or monitor a psychological condition or quantify a psychological process in a patient.

As used herein, the term "objective" psychological assessment can refer to the use of one or more quantitative measurements that are uninfluenced by the human perceiver/patient and/or administrator/clinician to provide an objective metric for an associated psychological process.

As used herein, the term "eye tracking" can refer to the process of electronically locating a point of a patient's gaze and/or following and recording the movement of the point of gaze. The terms "eye tracking" and "gaze tracking" can be used interchangeably herein.

As used herein, the term "remote" eye tracking can refer to a non-invasive detection of eye position and movement, without involving any attachments to the cornea. One example of remote eye tracking technology can be provided by Tobii Inc. to collect remote eye tracking data during viewing of visual stimuli.

As used herein, the term "paradigm" can refer to a typical example or pattern, such as a specific pattern of visual stimuli that are used during an objective psychological analysis.

As used herein, the term "medical professional" can refer to can refer to any clinician involved in medical care of a patient including, but not limited to, physicians, medical students, nurse practitioners, nurses, and technicians. The term "medical professional" can also refer to a skilled professional who administers the test, including an engineer, a technician, or the like.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient", "user", and "subject" can be used interchangeably herein.

As used herein, the term "visual stimulus" is intended to refer to any stimulus that contains visual elements (e.g., a still image, a video clip, an animated image, etc.). Accordingly, a visual stimulus, as used herein, can contain additional non-visual elements, such as auditory elements, As used herein, the term "gaze tracking data" can include any data that can be retrieved or derived from information provided from a gaze tracking device. This can include parameters derived from tracking the location of the patient's gaze, such a dwell time on a portion of a stimulus, a fixation time on a portion of the stimulus, a fixation count, a number of gaze visits, and a number of saccades of the patient, as well as parameters derived from one or more cameras associated with the gaze tracking device, including parameters derived from images and video of the patient's pupils.

As user herein, the term "image" refers to an array of digital values representing the output of a device that detects light within a known frequency band with the infrared, visible, or ultraviolet ranges. An image can be, for example, a single image or a frame of a video captured at a camera or similar light detecting device.

The present disclosure relates generally to a psychological assessment, during which a skilled professional can use the techniques and tools of psychology to quantify one or more psychological processes associated with a patient. Examples of such processes can include the ability of a patient to attend to a visual stimulus, the ability or tendency of a patient to attend to socially or emotionally relevant visual stimulus, ability to attend to a stimulus that corresponds to a verbal concept (e.g., looking at a stimulus that is named in an auditory cue). It will be appreciated that indices representing these processes can be used to quantify an ability of a patient in a particular field or skill, diagnose or monitor a psychological condition (e.g., autism spectrum disorder (ASD), anxiety disorder, attention deficit hyperactivity disorder (ADHD), language disorder, and the like) in a patient, or otherwise access the mental state of a patient. Traditional psychological assessments have suffered from rater bias, leading to inconsistent diagnosis and monitoring, due to the use of only subjective, qualitative measurements, such as patient/parent interview and behavioral observation, which involve perceptions of the individuals involved. The present disclosure provides an objective means for psychological assessment, which is based on quantitative measurements of a patient's remote eye gaze and similar objective data, which are not influenced by subjective perspectives or skewed by rater bias.

Assessments for psychological conditions for children are particularly difficult, as it can be challenging to keep the attention of a child, particularly a young child, for the entire length of an assessment process. Accordingly, the present invention relates to systems and methods that execute an adaptive psychological assessment based on exposing a patient to a set of visual stimuli and measuring a patient's gaze via remote eye tracking. The specific visual stimuli presented to the user can be selected according to the remote eye tracking measured for previous stimuli, allowing for the specific stimuli and their sequence to be adapted for each patient. This allows for the assessment to be streamlined, as stimuli can be selected in increase the information content provided by each stimulus. Accordingly, the set of visual stimuli can include a first set of stimuli that is presented to all patients, and a second set of stimuli that is selected according the response of the patient to the first set of stimuli.

One aspect of the present disclosure can include a system 100 that can execute an adaptive psychological assessment. A number of psychological processes in patients can be evaluated by tracking in eye gaze. Accordingly, the objective psychological assessment can be based on measuring a patient's gaze via remote eye tracking and can be used to create objective eye gaze-based indices, which can inform clinical judgment for different psychological processes.

Figure 1:
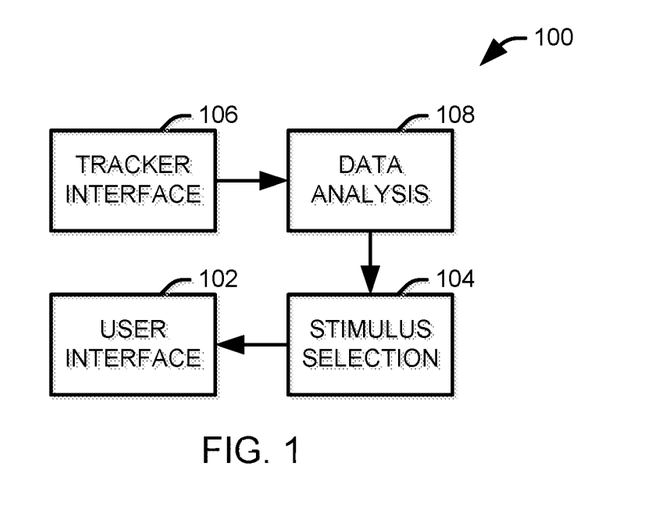
FIG. 1 illustrates one example a computer-implemented system for executing an adaptive psychological assessment.

FIG. 1 illustrates one example a computer-implemented system 100 for executing an adaptive psychological assessment. In particular, the system 100 determines a value for each of a plurality of indices, each representing a psychological condition. The system 100 includes a user interface 102 that provides a selected visual stimulus to a patient at an associated display. For example, the user interface 102 can include appropriate software for displaying audiovisual material to a user at associated output devices, as well as one or more appropriate interfaces for receiving selected stimuli from a stimulus selector 104. The user interface 102 can include, for example, appropriate drivers for interfacing with a display, speakers, a touchscreen, headphones, a mobile device, or a similar device configured for audiovisual display.

A tracker interface 106 receives gaze tracking data from a remote eye tracking device in response to the selected stimulus being displayed to a user. The gaze tracking data can include one or more of a dwell time on a portion of the stimulus, a fixation time on a portion of the stimulus, a fixation count, a number of gaze visits, and a number of saccades of the patient. For example, for a stimulus presented as images of the faces of a smiling man and a frowning woman, the tracker interface can determine the dwell and/or fixation time on each face, the number of times the gaze shifts between the two stimuli, and the amount of time for which the user did not gaze at either image. A data analyzer 108 that determines a deviation of the gaze tracking data from a standard response. In one implementation, the deviation is determined as a difference between an average value associated with the stimulus for the gaze tracking parameter and the value of the gaze tracking parameter for the patient divided by a standard deviation associated with the stimulus for the gaze tracking parameter. The data analyzer 108 then adjusts a score and an associated confidence value for at least one of the plurality of indices based on the determined deviation of the gaze tracking data from the standard response.

The stimulus selector 104 that selects a visual stimulus for display via the user interface 102, with at least some stimuli for display are selected based on the confidence values of the plurality of indices. In one implementation, the stimulus selector 104 selects stimuli from a first set of stimuli that are provided to all patients until all of the first set of stimuli is selected before selecting the new visual stimulus based on the confidence values of the plurality of indices. In the illustrated system, the stimulus selector 104 selects a stimulus that provides the most information, that is, has a largest discriminative value, for the index having a lowest confidence value. This can continue until each index has reached a threshold confidence value. It will be appreciated that both the scores for the plurality of indices as well as the gaze tracking parameters for the individual stimuli can be provided to an associated server for retrieval by a user or for revising the discriminative value of individual stimuli.

Figure 2:
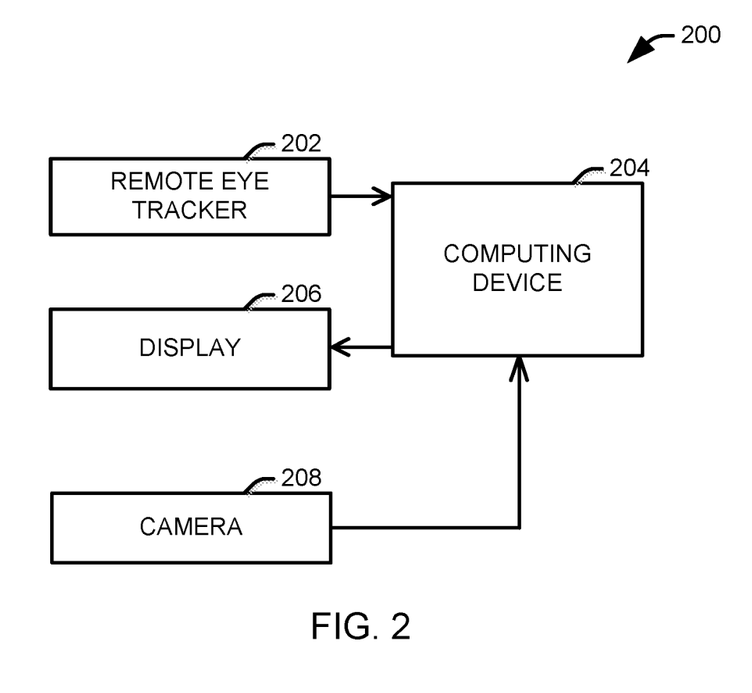
FIG. 2 illustrates one implementation of a system for adaptive assessment of psychological processes.

FIG. 2 illustrates one implementation of a system 200 for adaptive assessment of psychological processes. The system 200 can include at least a remote eye tracker device 202, a computing device 204, and a display device 206 that can operate together to execute the objective psychopathological assessment. The computing device 204 can deliver one or more visual stimuli to the display device 206, which can display the visual stimuli to a patient. The display device 206, which can display the various visual stimuli when instructed by the computing device 204, can include, for example, a computer monitor, a touch screen monitor, a smartphone monitor, a television monitor, or any other type of device that can display the visual stimuli to the patient. The system 200 can also include a camera 208 that records the facial expression of the user when the stimuli are presented.

While the patient views the visual stimuli on the display device 206, the remote eye tracker device 202 can record and collect data related to the patient's eye gaze remotely and the camera 208 can capture images of the patient's face. The remote eye tracker device 202 can be embodied, for example, in a device incorporating infrared projectors that create a pattern of light on the patient's eyes, cameras that take high resolution images of the eyes and the projected pattern, and processing software for determining the position and gaze point of the eyes. One example of such as system can be found in U.S. Pat. No. 7,752,008, which is hereby incorporated by reference. The remote eye tracker 202 device can send the data to the computing device 204 for further analysis. In some instances, the remote eye tracker device 202 can perform pre-processing functions on the data before it is sent to the computing device 204. In other instances, the remote eye tracker device 202 sends raw data to the computing device 204, and the computing device performs all of the processing of the data.

Figure 3:
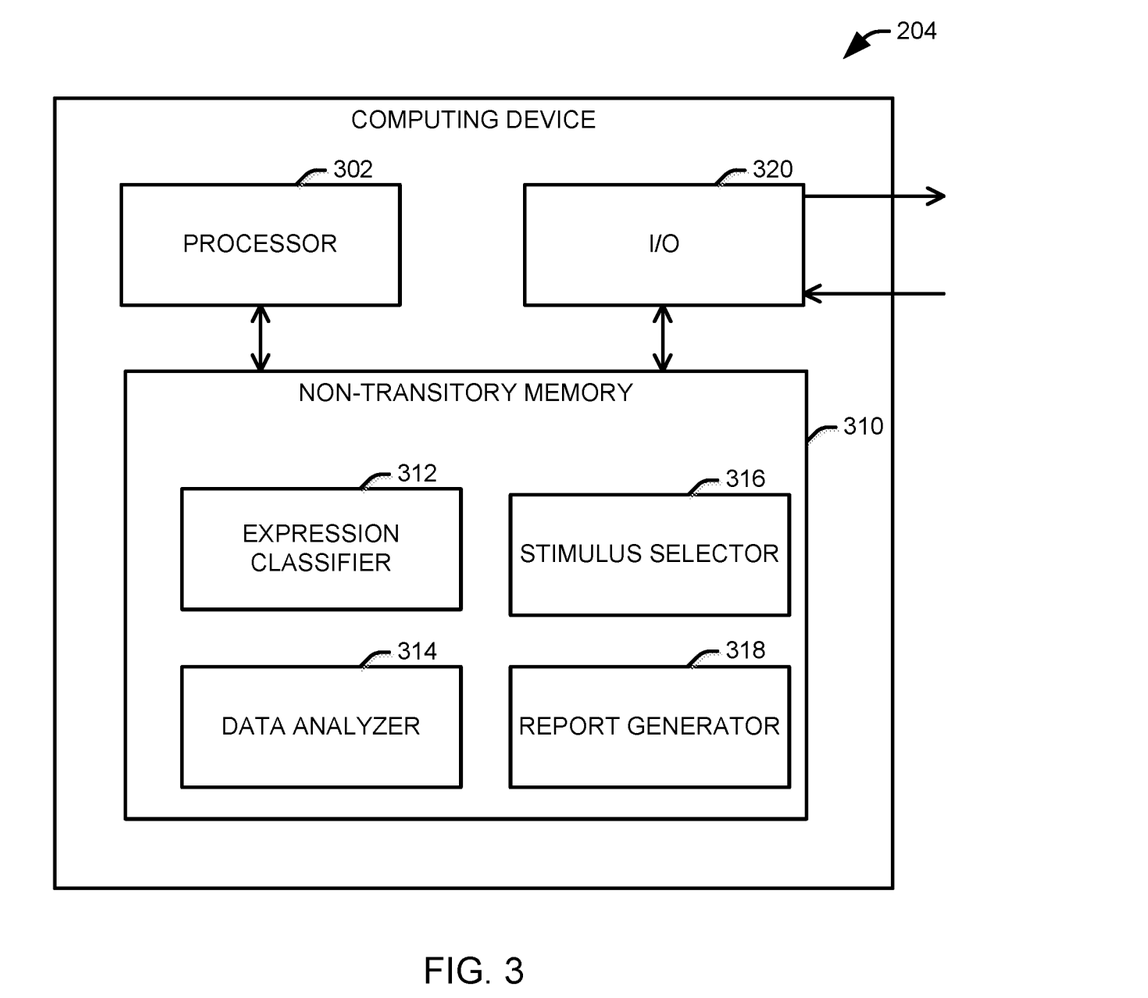
FIG. 3 is a diagram of an example of a computing device that can be used by the system in FIG. 2.

An example of the computing device 204 is illustrated in FIG. 3. The computing device 204 can include a processor 302 and a non-transitory memory 310. In the illustrated implementation, the non-transitory memory 310 includes a facial expression classifier 312, data analyzer 314, a stimulus selector 316, and a report generator 318, which can facilitate the psychological assessment based on measuring a patient's gaze via remote eye tracking. The facial expression classifier 312, the data analyzer 314, the stimulus selector 316, and the report generator 318 can be implemented as computer program instructions stored in the non-transitory memory 310. The processor 302 can be any type of device that can facilitate the execution of computer program instructions to perform one or more acts of the objective psychological assessment. Additionally, the non-transitory memory 310 can store data related to the objective psychological assessment, including two or more sets of visual stimuli defined according to two or more different paradigms and the remote gaze data, as well as software interfaces for each of the remote eye tracker 202, the display 206, and the camera 208.

The non-transitory memory 310 can include one or more non-transitory media that can contain or store the program instructions for use by or in connection with the instruction or execution of the objective psychological assessment and the data. Examples of non-transitory media can include electronic, magnetic, optical, electromagnetic, infrared, or semiconductor systems, apparatuses or devices. More specific examples of non-transitory media can include any of the following: a portable computer diskette; a random access memory; a read-only memory; an erasable programmable read-only memory (or Flash memory); and a portable compact disc read-only memory.

The computing device 204 also can include an I/O interface 320 that can communicate with at least the display device 206 and the remote eye tracker device 202. For example, the I/O 320 can communicate the visual stimulus to the display device 206 and receive the gaze tracking data from the remote eye tracker device 202 and the facial images from the camera 208. Accordingly, the computing device 204 can communicate in any number of different protocols so that the I/O 320 can communicate with in the protocol (e.g., USB, serial connection, parallel connection, Firewire connection, or the like) accepted by the display device and the remote eye tracker device 202.

The I/O 320 can send one or more visual stimuli to the display device 206 for display to the patient. The computing device 204 can receive gaze tracking data from the remote eye tracker device 202 in response to the visual stimulus being displayed to a user, and the camera 208 can record the face of the user during presentation of the stimulus. The facial expression classifier 312 can evaluate the recorded data from the camera and/or recorded images or videos of the patient's pupils from the remote eye tracker device, to assign an emotional state to the user during the reaction to various stimuli as well as an overall emotional state for the entire procedure. For example, the user's reaction to the stimulus can be represented as one or more probability values for various affects provided by the facial expression classifier 312, and the user's deviation from a standard response can be determined as a difference or normalized difference between expected probabilities and those determined for the user.

It will be appreciated that the facial expression classifier 312 can be implemented by one or more machine learning models, each trained to generate a continuous or categorical value representing each of a set of one or more affect classes (e.g., interest, anger, fear, etc.) from one or more images of the user's face and/or pupils. Where multiple machine learning models are used, an arbitration element can be utilized to provide a coherent result from the plurality of models. The training process of a given classifier will vary with its implementation, but training generally involves a statistical aggregation of training data into one or more parameters associated with the output class. Any of a variety of techniques can be utilized for the classification algorithm, including support vector machines, regression models, self-organized maps, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

The data analyzer 314 can compare the user's reaction to the stimulus to a standard response, and characterize the user's deviation from the standard response. In one implementation, a gaze fixation is determined when the user gazes at a particular location on the screen for a predetermined amount of time, in one example, on the order of sixty milliseconds, without a significant interruption. In this implementation, a significant interruption occurs when a gaze is detected for a specific length of time (e.g., on the order of twenty milliseconds) at a different location within a threshold distance of the location or for any length of time at a location beyond the threshold distance. The duration of the gaze fixation for each valid gaze is calculated from the beginning of the gaze until an interruption occurs.

In one implementation, the data analyzer 314 determines a number of gaze fixations and duration of fixations with respect to specific regions of interest for each stimulus. The absolute measurements and the variation of these measurements with respect to the stimuli presented is used to determine the deviation from the standard response, for example, as a distance metric (e.g., Euclidean, Manhattan, or Mahalanobis). Specifically, values that can be used in evaluating the user's response, and thus the deviation from the standard response, can include the number of gaze fixations, the durations of the gaze fixations, the locations of the gaze fixations, whether the location for each fixation lies inside or outside pre-defined region associated with stimuli, the duration between gaze fixations, and the validity of gaze to the stimuli.

The data analyzer 314 can also generate a number of parameters from images and video of the patient's pupil acquired during gaze tracking. Appropriate gaze data from these images can include a tonic pupil size, which measures the overall size of the pupil. This is a measure of autonomic activation in the norepinephrine-locus coeruleus system, and can be used in along with the images from the camera 208 at the facial expression classifier 312 in determining an affect of the patient. A pupillary light reflect represents a rapid change in pupil diameter (constriction and redilation) in response to a light flash. This also measures autonomic activation, and can be used in a manner similar to the tonic pupil size. A phasic pupil change represents a change in the pupil in response to stimuli. This is expected to be correlated with attention and interest, and can be used as a stand-alone gaze parameter in generating the various indices or as a multiplier applied to one or more other gaze parameters generated from a given visual stimulus.

In addition, an affect of the patient in response to the stimulus, as determined at the facial expression classifier 312 can be compared to an expected response to the portion of the stimulus that the user is observing in determining the deviation of the user's response from a standard response. In one implementation, the determined affect can be used in calculating the metric characterizing the user's deviation from a standard response or as a multiplicative factor increasing or decreasing the deviation based on the reported affect or lack of affect.

In one example, the data can be standardized by subtracting each individual data value from a mean for a control population representing the standard response and dividing by a standard deviation of the control population. From these values, a plurality of indices can be calculated, each providing a measure of a specific psychological process. For example, the index can be calculated as a measure of central tendency (e.g., arithmetic mean, geometric mean, or median) for the standardized data, as an output of a machine learning model, such as those described above for use in the facial expression classifier, or as a linear combination of the standardized data. In one example, the indices include an autism risk index, a general autism symptom index, an autism symptom index specific to social communication interaction, a general attention index, and an autism symptom index specific to restricted and repetitive behavior. Each presented stimulus can be associated with one or more of the plurality of indices, and the patient's reaction to the stimulus, or more specifically, the deviation of the patient's reaction from the standard reaction, can be used to determine the score for each index. In one example, the discriminative power of each stimulus with respect to each index can be binary, with stimuli that are useful for a given index having a weight of one for that index and stimuli that not useful for computing the index given a zero. In another example, each stimulus can be assigned a discriminative value according to testing data, derived, for example, from a Cohen d effect size The stimulus selector 316 can be configured to select stimuli to efficiently achieve a threshold confidence level for each of the plurality of indices. In one example, the confidence value for a given index can be computed as a confidence interval for each index given the deviations from normal standard responses calculated at the data analyzer 314. The breadth of the confidence interval for each index can be used as a measure of the confidence in the index and compared to a threshold value to determine when the threshold confidence in a given index has been reached or, when an index has a threshold score used for diagnosis of a psychological condition, a threshold confidence is reached when the confidence interval excludes the threshold score.

In one implementation, the stimuli can be applied in sets associated with the various indices, such that only stimuli associated with a first index are presented until the desired level of confidence is reached for that index. Once the desired level of confidence is achieved, only stimuli associated with the second index are presented until a threshold level of confidence is achieved for that index, and so forth. In this implementation, the stimuli can be selected in terms of decreasing discriminative value for each index. It will be appreciated that some stimuli are intended to measure more severe presentations of psychological conditions represented by a given index. Where the user exhibits significant deviations from standard values for these stimuli, the weight assigned to these stimuli can be enhanced, as it is generally indicative of significant presentation of symptoms. Similarly, where there is a threshold value for a diagnosis of a given psychological condition, the confidence value for the index can represent a likelihood that the user exhibits the psychological condition, and significant deviation from standard values for these stimuli can also be weighted heavily in generating the confidence value.

Additionally or alternatively, the stimulus selector 316 can select stimuli in order by discriminative value, that is, the general tendency of each stimulus to increase confidence in its associated index or indices. The discriminative value of each stimulus can be estimated over time based on patient responses to the stimulus at the system 200. In particular, the detected affect at the facial expression classifier 312 can be used to select additional stimuli. For example, if the user reacts positively to a social stimulus intended to provoke a positive response, such as a smiling face, additional stimuli expected to elicit the same or different emotional responses (e.g., a person laughing or a person frowning) can be presented to increase confidence that the patient is truly responding to the social content of the stimulus. In one implementation, discussed in more detail in FIG. 4, the patient responses to stimuli can be aggregated across multiple client systems at a server to improve the estimated discriminative values for the stimuli. These estimated values can then be distributed to the various clients or local servers controlling the clients to refine the selection sequence at the stimulus selector 31.

Once the indices are determined, the report generator 318 can provide a report for clinicians to interpret the different scores and indices. For example, the report can analyze various levels of ability across a number of psychological processes, as well as the patient's likelihood of having a specific psychological condition based on the gaze tracking data and recorded facial expressions. In one example, the report can include a comparison, conducted by the report generator 318, between the indices with expected normative levels. In another example, the report from the report generator 32 can display each index as a standard score (e.g., scaled to a mean of 100 and a standard deviation of 15) relative to age-adjusted population norms. Text descriptions can also be provided to describe the range the score falls into. In yet another example, the report can include figures displaying the relative level of the score and its position within the score ranges. Indeed, the report can include information, determined objectively, that can be used to associate the patient with a given psychological condition, diagnose a psychopathology, or monitor symptom progression with a psychopathology.

It will be appreciated that, for some psychological processes, additional data can be helpful in accessing the mental state of the patient. To that end, the system 200 can include additional sources of data, including but not limited to a microphone, motion sensors worn by the patient or incorporated into a seat used by the patient, and biometric monitoring equipment, such as heart rate monitors, galvanic skin response sensors, respiratory monitors, or other such sensors. Each sensor can have appropriate software at the computing device 204 to evaluate the received data and determine psychologically relevant data for the patient. Like the facial recognition data, this additional data can be used for either or both of evaluating the patient's deviation from a normal response to a stimulus or for guiding the selection of additional stimuli, for example, to maximize a discriminative value of a next selected stimulus for one or more indices of interest.

Figure 4:
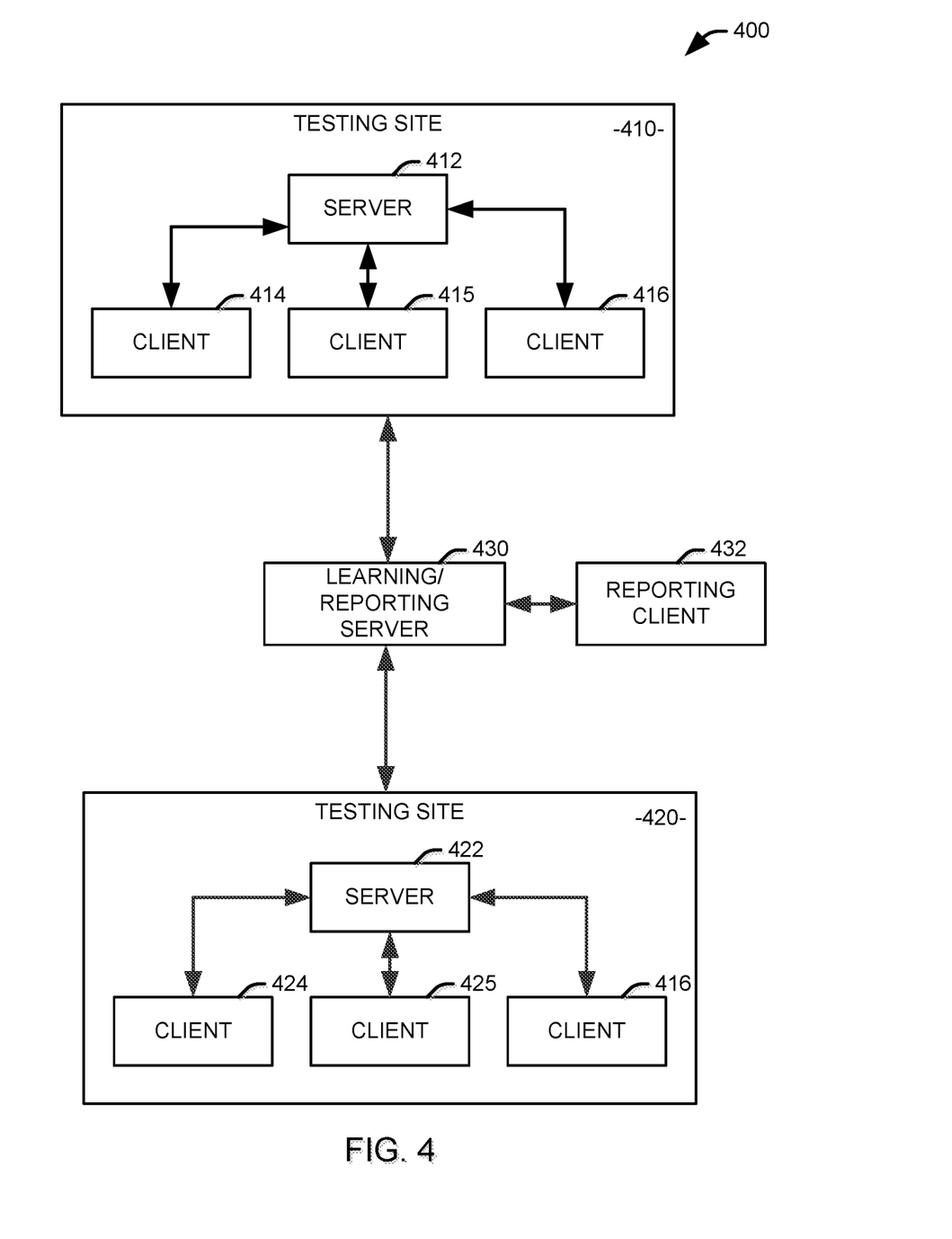
FIG. 4 illustrates one implementation of a system in which responses at multiple testing sites are aggregated at a learning/reporting server.

FIG. 4 illustrates one implementation of a system 400 in which responses at multiple testing sites 410 and 420 are aggregated at a learning/reporting server 430. Each testing site 410 and 420 includes a local server 412 and 422 and a plurality of clients 414-416 and 424-426. The clients 424-426 collect subject identification, present visual stimuli, collect raw gaze data, collect raw facial expression data, and determine data validity. Accordingly, looking at the system of FIGS. 2 and 3, a given client (e.g., 414) includes the remote eye tracker 202, the display 206, the camera 208, and a computing device 204 configured to receive raw data from the eye tracker and the camera via the I/O 320 and a network interface to transfer valid data to the local server (e.g., 412).

The local servers 412 and 422 include the software instructions for at least the expression classifier 312, the data analyzer 314, and the stimulus selector 316. Accordingly, the local servers 412 and 422 validate the eligibility of patients at their associated clients, evaluate gaze data, and signal the clients with information regarding appropriate visual stimuli based on previous responses, and signal the client when the threshold confidence value is achieved for all indices and the testing can conclude. The clients 414-416 and 424-426 present additional visual stimuli based on the signaling from the local server until signaled to conclude the test. The learning/reporting server 430 collects gaze data and facial expression data from all of the local servers 412 and 422, stores data, computes measurements, compiles reports, and distributes reports, performing at least the function of the report generator 318 of FIG. 3. The learning/reporting server 430 can also update selection criteria for visual stimuli at the local servers 412 and 422 based on data collected across all testing sites 410 and 420. In particular, the discriminative values for each stimulus with respect to each index can be updated as new data is received, and these values can be provided back to the stimulus selector associated with each client 414-416 and 424-426. One or more reporting clients 432 can communicate with the learning/reporting server 430 to provide access to reporting and administration of overall system.

Figure 5:
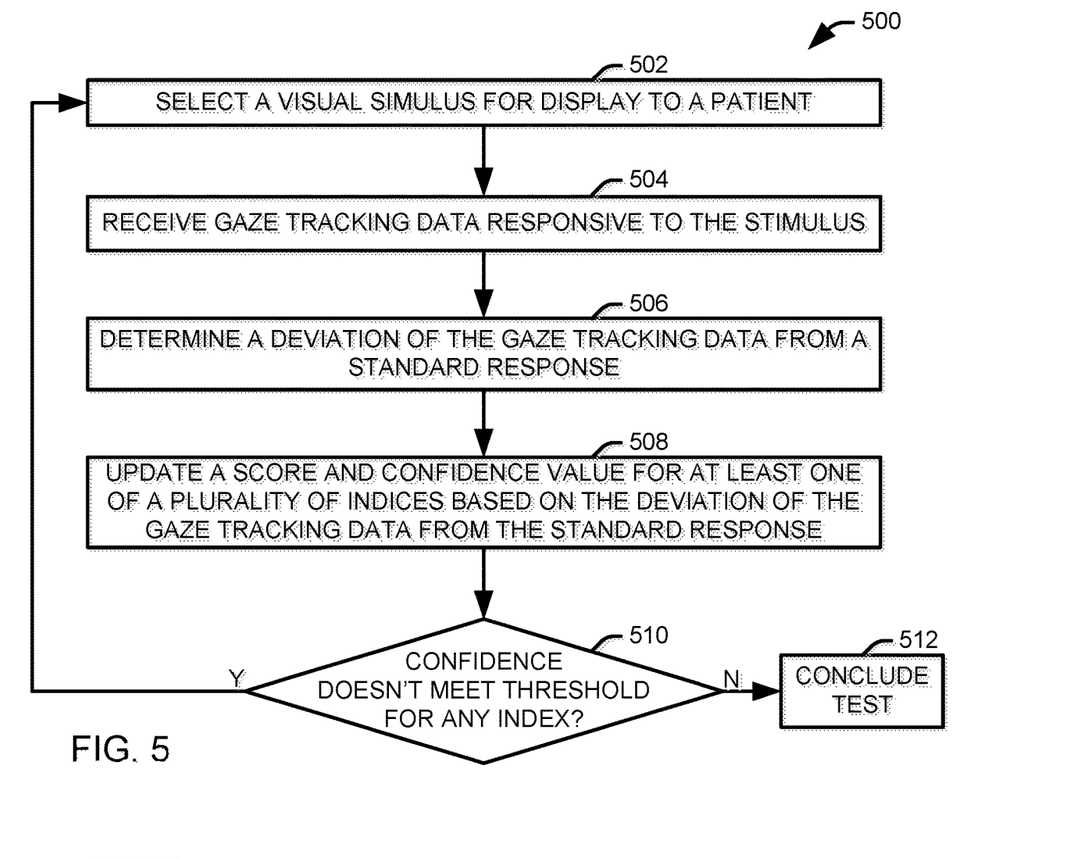
FIG. 5 illustrates a method for determining a plurality of indices representing psychological processes.

Another aspect of the present disclosure can include a method 500 for executing an adaptive psychological assessment based on measuring a patient's gaze via remote eye tracking, as shown in FIG. 5. As an example, the method 500 can be accomplished using the system 200, as shown in FIG. 2, that includes a remote eye tracker device 202, a display device 206, and a computing device 204 that includes a non-transitory memory and a processor. For example, acts of the method 500 can be implemented by computer program instructions that are stored in the non-transitory memory and provided to a processor of a general purpose computer, special purpose computer, and/or other programmable data processing apparatus to produce a machine, such that the instructions, which execute via the processor of the computing device 204, create mechanisms for implementing the steps/acts specified in the flowchart blocks and/or the associated description. In other words, the processor can access the computer-executable instructions that are stored in the non-transitory memory.

For purposes of simplicity, the method 500 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 500.

FIG. 5 illustrates a method 500 for determining a plurality of indices for evaluating psychological processes, which can include, for example, aptitudes for a particular skill, tendencies toward a particular mental state, or psychopathologies, such as for autism spectrum disorder (ASD), anxiety disorder, attention deficit hyperactivity disorder (ADHD), language disorder, and the like. In one implementation, the plurality of indices include one or more of an autism risk index, a general autism symptom index, an autism symptom index specific to social communication interaction, and an autism symptom index specific to restricted and repetitive behavior. In some instances, the method 500 can be performed using the system 200 of FIG. 2, in which the computing device 204 communicates with the remote eye tracking device 202, which records eye gaze data, and the display device 206, which displays visual stimuli to a patient, to determine the aggregate psychopathological index objectively.

At 502, a visual stimulus is selected and provided to the patient at the display. At 504, gaze tracking data is received from a remote eye tracking device in response to the visual stimulus being displayed to a user. In one example, the gaze tracking data includes parameters representing at least two of a dwell time on a portion of the stimulus, a fixation time on a portion of the stimulus, a fixation count, a number of gaze visits, and a number of saccades of the patient. As discussed previously, the gaze tracking data can be used, in some embodiments, in combination with facial imaging, recorded audio, or biometric monitoring, and these can be collected simultaneously with the gaze tracking data. For example, a face of the patient can be recorded as at least one image while the visual stimulus is provided at the display, an emotional state can be assigned to the patient from the at least one image, and any deviation of the assigned emotional state from an expected response can be determined and applied to adjust the score and confidence value for at least one of the plurality of indices based on the determined deviation of the assigned emotional state from the expected response.

At 506, a deviation of the gaze tracking data, and in some implementations, the other collected data, from a standard response is determined. For example, various metrics can be determined from the collected data, and a distance value can be calculated representing the variation of these metrics from the values associated with a standard response. In one implementation, the deviation is calculated as an average value across a plurality of control patients for each of the plurality of gaze tracking parameters. At 508, a score and the associated confidence value for at least one of the plurality of indices can be adjusted based on the determined deviation of the collected data from the standard response. In one implementation, representative statistics, such as a standard deviation, can be calculated across the determined deviation values for the gaze tracking data to measure the confidence in a given index value. At 510, it is determined if the confidence value for one of the plurality of indices meets a threshold value. If not (N), the test is concluded at 512, and respective scores for the plurality of indices are provided to a user.

If a confidence value for one of the plurality of indices does not meet the threshold value (Y), the method returns to 502 to select a new stimulus to present to the patient. For example, each visual stimulus has an associated discriminative value for each index, and the new visual stimulus is selected as a stimulus having a highest discriminative value for an index having the lowest confidence value. In this implementation, the system can begin by selecting from a first set of stimuli that are provided to all patients exhausted before selecting new visual stimuli according to the confidence values of the plurality of indices. In one example, a confidence value is generated for each index as a measure of deviation across values of the gaze tracking data for the patient.

Figure 6:
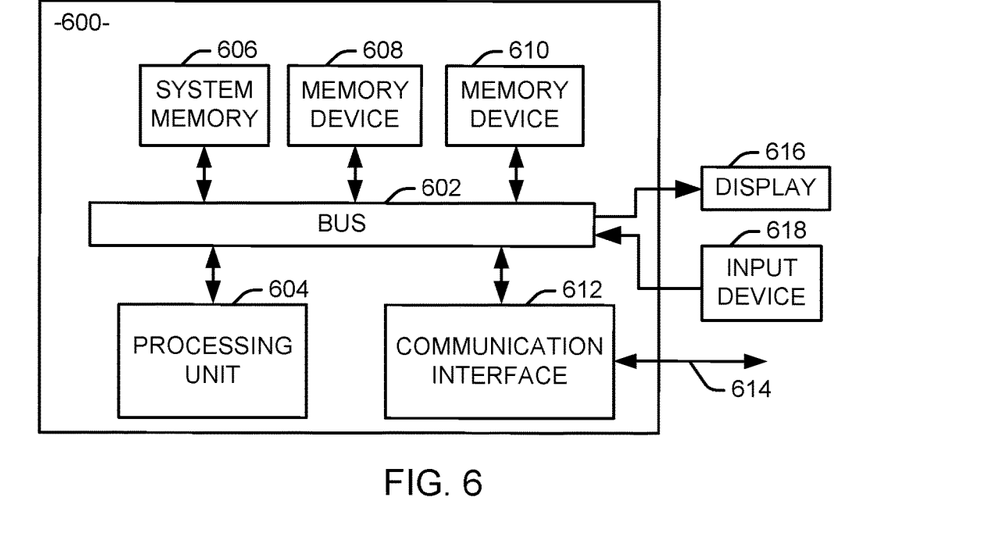
FIG. 6 is a schematic block diagram illustrating an exemplary system of hardware components capable of implementing examples of the systems and methods disclosed herein.

FIG. 6 is a schematic block diagram illustrating an exemplary system 600 of hardware components capable of implementing examples of the systems and methods disclosed herein. The system 600 can include various systems and subsystems. The system 600 can be a personal computer, a laptop computer, a workstation, a computer system, an appliance, an application-specific integrated circuit (ASIC), a server, a server BladeCenter, a server farm, etc.

The system 600 can include a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard, touch screen, and/or a mouse). The system bus 602 can be in communication with the processing unit 604 and the system memory 606. The additional memory devices 608 and 610, such as a hard disk drive, server, standalone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core.

The additional memory devices 606, 608, and 610 can store data, programs, instructions, database queries in text or compiled form, and any other information that may be needed to operate a computer. The memories 606, 608 and 610 can be implemented as computer-readable media (integrated or removable), such as a memory card, disk drive, compact disk (CD), or server accessible over a network. In certain examples, the memories 606, 608 and 610 can comprise text, images, video, and/or audio, portions of which can be available in formats comprehensible to human beings. Additionally or alternatively, the system 600 can access an external data source or query source through the communication interface 612, which can communicate with the system bus 602 and the communication link 614.

In operation, the system 600 can be used to implement one or more parts of a system for assessing a psychological condition of a user in accordance with the present invention. Computer executable logic for implementing the psychological assessment system resides on one or more of the system memory 606, and the memory devices 608 and 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system that provides a psychological assessment comprising:
   a display;
   a non-transitory memory storing machine-readable instructions; and
   a processor to access the non-transitory memory and execute the machine-readable instructions, the machine-readable instructions comprising:
      a user interface that provides a selected visual stimulus to a patient at an associated display, the selected visual stimulus being associated with at least one of a plurality of indices, each representing a measure of a specific psychological process and having a score representing the measure of the specific psychological process and an associated confidence value for the score;
      a tracker interface that receives gaze tracking data, comprising a plurality of gaze tracking parameters, from a remote eye tracking device in response to the selected stimulus being provided to the patient;
      a data analyzer that determines a deviation of the gaze tracking data from a set of standard responses associated with the plurality of gaze tracking parameters for each of the plurality of gaze tracking parameters and adjusts the score and the associated confidence value for the score for each of the at least one of a plurality of indices based on the determined deviation of the gaze tracking data from the standard response for each of the plurality of gaze tracking parameters; and
      a stimulus selector that selects a new visual stimulus based on the confidence values of the plurality of indices.

2. The system of claim 1, further comprising a camera that records a face of the patient as at least one image while the visual stimulus is provided, the executable instructions comprising an expression classifier assigns an emotional state to the patient from the at least one image.

3. A system comprising:
   a plurality of local testing sites, each comprising the system of claim 1; and
   a remote server that aggregates data from the plurality of local testing sites and provides feedback to the local testing sites, such that the selection of the new visual stimulus depends on the feedback.

4. The system of claim 3, wherein the stimulus selector selects from a first set of stimuli that are provided to all patients until all of the first set of stimuli are selected before selecting the new visual stimulus based on the confidence values of the plurality of indices.

5. The system of claim 4, wherein each visual stimulus of the first set of stimuli has an associated discriminative value, representing the general tendency of each stimulus to increase confidence in a given index, for each index of the plurality of indices, and the stimulus selector determines an index of the plurality of indices having a score with a lowest associated confidence value and selects the new visual stimulus as a stimulus from a second set of stimuli having a highest discriminative value for the index having the score with the lowest associated confidence value.

6. The system of claim 5, wherein the remote server updates discriminative value for each stimulus for at least one of the plurality of indices using data from the plurality of remote testing sites and provides the updated discriminative value for each stimulus to the stimulus selector at each of the plurality of remote testing sites.

7. The system of claim 1, wherein the gaze tracking data comprises at least one of a dwell time on a portion of the stimulus, a fixation time on a portion of the stimulus, a fixation count, a number of gaze visits, and a number of saccades of the patient.

8. The system of claim 1, wherein the data analyzer determines the deviation of the gaze tracking data for each of the plurality of gaze tracking parameters as a ratio of a difference between an average value associated with the stimulus for the gaze tracking parameter and the value for the patient to a standard deviation associated with the stimulus for the gaze tracking parameter.

9. The system of claim 1, wherein the specific psychological process represents one of an autism spectrum disorder, an anxiety disorder, an attention deficit disorder, and a language disorder.

10. A method, comprising:
    selecting an initial visual stimulus as a selected visual stimulus, the selected visual stimulus being associated with at least one of a plurality of indices, each representing a measure of a specific psychological process and having a score representing the measure of the specific psychological process and an associated confidence value for the score;
    iteratively performing the following steps until associated confidence values for each of a plurality of indices meet a threshold value:
       providing the selected visual stimulus at the display;
       receiving gaze tracking data, comprising a plurality of gaze tracking parameters, from a remote eye tracking device in response to the selected stimulus being displayed to a patient;
       determining a deviation of the gaze tracking data from a set of standard responses associated with the plurality of gaze tracking parameters for each of the plurality of gaze tracking parameters;
       adjusting the score and the associated confidence value for the score for each of the at least one of the plurality of indices based on the determined deviation of the gaze tracking data from the standard response for each of the plurality of gaze tracking parameters; and
       selecting a new visual stimulus based on the confidence values of the plurality of indices; and
    providing respective scores for the plurality of indices to a user.

11. The method of claim 10, wherein the plurality of gaze tracking parameters includes at least two of a dwell time on a portion of the stimulus, a fixation time on a portion of the stimulus, a fixation count, a number of gaze visits, and a number of saccades of the patient.

12. The method of claim 11, wherein the set of standard responses comprises an average value across a plurality of control patients for each of the plurality of gaze tracking parameters.

13. The method of claim 10, further comprising:
recording a face of the patient as at least one image while the visual stimulus is provided at the display;
assigning an emotional state to the patient from the at least one image;
determining any deviation of the assigned emotional state from an expected response; and
adjusting the score and confidence value for the at least one of the plurality of indices based on the determined deviation of the assigned emotional state from the expected response.

14. The method of claim 10, wherein the plurality of indices include at least one of an autism risk index, a general autism symptom index, an autism symptom index specific to social communication interaction, and an autism symptom index specific to restricted and repetitive behavior.

15. A non-transitory computer readable medium storing machine-readable instructions that are executable by a processor, the machine-readable instructions comprising:
a user interface that provides a selected visual stimulus to a patient, the selected visual stimulus being associated with at least one of a plurality of indices, each representing a measure of a specific psychological process and having a score representing the measure of the specific psychological process and an associated confidence value for the score;
a tracker interface that receives gaze tracking data, comprising a plurality of gaze tracking parameters, from a remote eye tracking device in response to the selected stimulus being displayed to a user;
a data analyzer that determines a deviation of the gaze tracking data from a set of standard responses associated with the plurality of gaze tracking parameters for each of the plurality of gaze tracking parameters and adjusts the score and the associated confidence value for the score for each of the at least one of a plurality of indices based on the determined deviation of the gaze tracking data from the standard response for each of the plurality of gaze tracking parameters; and
a stimulus selector that selects a new visual stimulus based on the confidence values of the plurality of indices.

16. The non-transitory computer readable medium of claim 15, the executable instructions further comprising a network interface that provides respective scores for the plurality of indices to a server, the scores for the plurality of indices being retrievable by a user from the server.

17. The non-transitory computer readable medium of claim 15, wherein the stimulus selector selects from a first set of stimuli that are provided to all patients until all of the first set of stimuli are selected before selecting the new visual stimulus based on the confidence values of the plurality of indices.

18. The non-transitory computer readable medium of claim 17, wherein each visual stimulus of the first set of stimuli has an associated discriminative value, representing the general tendency of each stimulus to increase confidence in a given index, for each index, and the stimulus selector determines an index of the plurality of indices having a lowest confidence value and selects the new visual stimulus as a stimulus from a second set of stimuli having a highest discriminative value for the index having the lowest confidence value.

19. The non-transitory computer readable medium of claim 15, wherein the data analyzer provides the deviation of the gaze tracking data from a standard response to a remote server that aggregates data from the data analyzer and at least one additional system and provides feedback to the stimulus selector, such that the selection of the new visual stimulus depends on the feedback.

* * * * *